(12) United States Patent
McGowan et al.

(10) Patent No.: US 10,722,690 B2
(45) Date of Patent: Jul. 28, 2020

(54) MEDICAL DEVICES WITH ANTITHROMBOGENIC COATINGS

(71) Applicant: BOSTON SCIENTIFIC SCIMED, INC., Maple Grove, MN (US)

(72) Inventors: Roger W. McGowan, Ostego, MN (US); Brice Lee Shireman, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 170 days.

(21) Appl. No.: 15/389,420

(22) Filed: Dec. 22, 2016

(65) Prior Publication Data
US 2017/0182295 A1    Jun. 29, 2017

Related U.S. Application Data

(60) Provisional application No. 62/271,706, filed on Dec. 28, 2015.

(51) Int. Cl.
*A61M 25/09*    (2006.01)
*A61B 5/0215*   (2006.01)
*A61B 5/00*     (2006.01)

(52) U.S. Cl.
CPC .......... *A61M 25/09* (2013.01); *A61B 5/0215* (2013.01); *A61B 5/02154* (2013.01); *A61B 5/6851* (2013.01); *A61M 2025/09133* (2013.01); *A61M 2025/09175* (2013.01); *A61M 2202/0478* (2013.01); *A61M 2205/3344* (2013.01)

(58) Field of Classification Search
CPC ... A61M 25/09; A61M 25/007; A61B 5/0215; A61B 5/02154; A61B 5/6851
USPC ......................................................... 600/561
See application file for complete search history.

(56) References Cited

U.S. PATENT DOCUMENTS

| 5,443,907 A | 8/1995 | Slaikeu et al. |
| 5,722,424 A | 3/1998 | Engelson |
| 6,918,873 B1 * | 7/2005 | Millar .................. A61B 5/0215 600/309 |
| 7,481,774 B2 | 1/2009 | Brockway et al. |

(Continued)

FOREIGN PATENT DOCUMENTS

| JP | H06-114111 A | 4/1994 |
| JP | H09135905 A | 5/1997 |

(Continued)

OTHER PUBLICATIONS

International Search Report and Written Opinion dated Mar. 13, 2017 for International Application No. PCT/US2016/068462.

*Primary Examiner* — Daniel L Cerioni
(74) *Attorney, Agent, or Firm* — Seager, Tufte & Wickhem, LLP

(57) ABSTRACT

Pressure sensing guidewires are disclosed. The pressure sensing guidewires may include a tubular member having a proximal portion and a distal portion. The distal portion may have a plurality of slots formed therein. The distal portion may have a first wall thickness along a first region and a second wall thickness smaller than the first wall thickness along a second region. A pressure sensor may be disposed within the distal portion of the tubular member and housed within the second region. An anti-thrombogenic coating may be disposed on an inner surface, an outer surface, or both of the second region of the distal portion of the tubular member.

19 Claims, 5 Drawing Sheets

(56) References Cited

U.S. PATENT DOCUMENTS

| | | |
|---|---|---|
| 8,298,156 B2 | 10/2012 | Manstrom et al. |
| 2002/0077596 A1* | 6/2002 | McKenzie ....... A61B 17/12109 604/104 |
| 2005/0209579 A1 | 9/2005 | Yacoubian et al. |
| 2009/0011117 A1* | 1/2009 | Nunez .............. A61F 2/07 427/2.31 |
| 2010/0145259 A1* | 6/2010 | Nash ............. A61B 17/32037 604/22 |
| 2012/0136244 A1 | 5/2012 | Manstrom et al. |
| 2012/0220883 A1 | 8/2012 | Manstrom et al. |
| 2013/0096409 A1 | 4/2013 | Hiltner et al. |
| 2013/0131523 A1 | 5/2013 | Suchecki et al. |
| 2013/0324864 A1 | 12/2013 | Manstrom et al. |
| 2013/0331714 A1 | 12/2013 | Manstrom et al. |
| 2014/0005543 A1 | 1/2014 | Burkett |
| 2014/0005558 A1 | 1/2014 | Gregorich |
| 2014/0005561 A1 | 1/2014 | Burkett |
| 2014/0058275 A1 | 2/2014 | Gregorich et al. |
| 2014/0066790 A1 | 3/2014 | Burkett et al. |
| 2014/0081244 A1 | 3/2014 | Voeller et al. |
| 2014/0180030 A1 | 6/2014 | Dorando |
| 2014/0180031 A1 | 6/2014 | Anderson |
| 2014/0236017 A1 | 8/2014 | Degertekin et al. |
| 2014/0275892 A1 | 9/2014 | Manstrom et al. |
| 2014/0276109 A1 | 9/2014 | Gregorich |
| 2014/0276117 A1 | 9/2014 | Burkett |
| 2014/0350414 A1 | 11/2014 | McGowan et al. |
| 2015/0032011 A1 | 1/2015 | McGowan et al. |
| 2015/0032066 A1 | 1/2015 | Burkett |
| 2015/0051499 A1 | 2/2015 | McGowan |
| 2015/0105673 A1 | 4/2015 | Gregorich |
| 2015/0141843 A1 | 5/2015 | Eberle et al. |
| 2015/0141854 A1 | 5/2015 | Eberle et al. |
| 2015/0173629 A1 | 6/2015 | Corl et al. |
| 2015/0173682 A1 | 6/2015 | Manstrom et al. |
| 2015/0223707 A1 | 8/2015 | Ludoph |
| 2015/0297807 A1 | 10/2015 | Leblanc et al. |

FOREIGN PATENT DOCUMENTS

| | | |
|---|---|---|
| JP | H1199201 A | 4/1999 |
| JP | 2010505534 A | 2/2010 |
| JP | 2015533542 A | 11/2015 |
| WO | 9953998 A1 | 10/1999 |
| WO | 2008024593 A2 | 2/2008 |
| WO | 2008042625 A2 | 4/2008 |
| WO | 2009120679 A1 | 10/2009 |
| WO | 2010030882 A1 | 3/2010 |
| WO | 2011159621 A2 | 12/2011 |
| WO | 2012155040 A1 | 11/2012 |
| WO | 2012173697 A1 | 12/2012 |
| WO | 2013055896 A1 | 4/2013 |
| WO | 2013177577 A2 | 11/2013 |
| WO | 2014005002 A1 | 1/2014 |
| WO | 2014005012 A1 | 1/2014 |
| WO | 2014005095 A1 | 1/2014 |
| WO | 2014035995 A1 | 3/2014 |
| WO | 2014036477 A1 | 3/2014 |
| WO | 2014043704 A1 | 3/2014 |
| WO | 2014100110 A2 | 6/2014 |
| WO | 2014100140 A1 | 6/2014 |
| WO | 2014149688 A1 | 9/2014 |
| WO | 2014190195 A1 | 11/2014 |
| WO | 2015013638 A1 | 1/2015 |
| WO | 2015013646 A1 | 1/2015 |
| WO | 2015023789 A1 | 2/2015 |
| WO | 2015057518 A1 | 4/2015 |
| WO | 2015113044 A1 | 7/2015 |
| WO | 2015116944 A1 | 8/2015 |

* cited by examiner

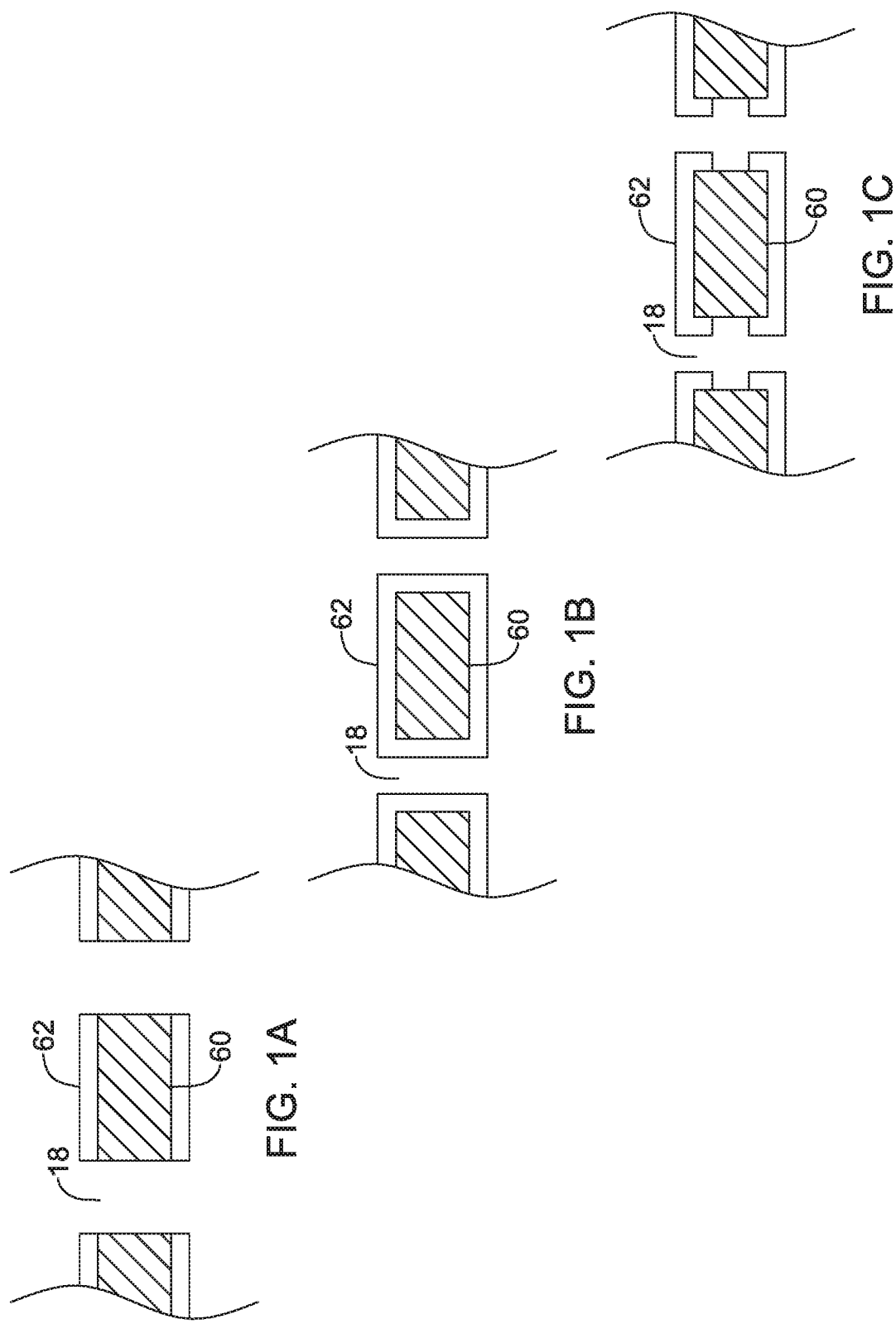

ABSTRACT# MEDICAL DEVICES WITH ANTITHROMBOGENIC COATINGS

CROSS-REFERENCE TO RELATED APPLICATIONS

This application claims the benefit of priority under 35 U.S.C. § 119 to U.S. Provisional Application No. 62/271,706, filed Dec. 28, 2015, the entirety of which is incorporated herein by reference.

TECHNICAL FIELD

The present disclosure pertains to medical devices, and methods for manufacturing medical devices. More particularly, the present disclosure pertains to blood pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices.

In a first example, a pressure sensing guidewire may comprise a tubular member having a proximal portion and a distal portion, wherein the distal portion may have a plurality of slots formed therein. The distal portion may have a first wall thickness along a first region and a second wall thickness smaller than the first wall thickness along a second region. The pressure sensing guidewire may further comprise a pressure sensor disposed within the distal portion of the tubular member and housed within the second region and an anti-thrombogenic coating disposed on an inner surface, an outer surface, or both of the second region of the distal portion of the tubular member.

Alternatively or additionally to any of the examples above, in another example, the anti-thrombogenic coating may comprise a hydrophilic coating.

Alternatively or additionally to any of the examples above, in another example, the hydrophilic coating may comprise a heparinized hydrophilic coating.

Alternatively or additionally to any of the examples above, in another example, the anti-thrombogenic coating may comprise a hydrophobic coating.

Alternatively or additionally to any of the examples above, in another example, the hydrophobic coating may comprise silicone.

Alternatively or additionally to any of the examples above, in another example, the hydrophobic coating may be disposed on the pressure sensor.

Alternatively or additionally to any of the examples above, in another example, the pressure sensing guidewire may further comprise one or more apertures formed in the second region of the distal portion.

Alternatively or additionally to any of the examples above, in another example, the second region of the distal portion may be free from the plurality of slots.

Alternatively or additionally to any of the examples above, in another example, the pressure sensor may be positioned proximal to the one or more apertures.

Alternatively or additionally to any of the examples above, in another example, the anti-thrombogenic coating may extend at least partially along a sidewall of the one or more apertures.

Alternatively or additionally to any of the examples above, in another example, the second region of the distal portion may include at least one of the plurality of slots formed therein.

Alternatively or additionally to any of the examples above, in another example, the anti-thrombogenic coating may extend at least partially along a sidewall of the at least one of the plurality of slots.

Alternatively or additionally to any of the examples above, in another example, the anti-thrombogenic coating may extend along an entire length of a sidewall of the at least one of the plurality of slots.

Alternatively or additionally to any of the examples above, in another example, the pressure sensor may be an optical pressure sensor.

Alternatively or additionally to any of the examples above, in another example, the first region of the distal portion may be disposed proximal to the second region of the distal portion.

In another example, a pressure sensing guidewire may comprise a tubular member having a proximal portion and a distal portion, wherein the distal portion may have a plurality of slots formed therein. The distal portion may have a first wall thickness along a first region and a second wall thickness smaller than the first wall thickness along a second region. The pressure sensing guidewire may further comprise a pressure sensor disposed within the distal portion of the tubular member and housed within the second region and an anti-thrombogenic coating disposed on an inner surface of the second region of the distal portion of the tubular member.

Alternatively or additionally to any of the examples above, in another example, the anti-thrombogenic coating may comprise a hydrophilic coating.

Alternatively or additionally to any of the examples above, in another example, the hydrophilic coating may comprise a heparinized hydrophilic coating.

Alternatively or additionally to any of the examples above, in another example, the anti-thrombogenic coating may comprise a hydrophobic coating.

Alternatively or additionally to any of the examples above, in another example, the hydrophobic coating may comprise silicone.

Alternatively or additionally to any of the examples above, in another example, hydrophobic coating may be disposed on the pressure sensor.

Alternatively or additionally to any of the examples above, in another example, the first region of the distal portion may be disposed proximal to the second region of the distal portion.

Alternatively or additionally to any of the examples above, in another example, the pressure sensing guidewire may further comprise one or more apertures formed in the second region of the distal portion.

Alternatively or additionally to any of the examples above, in another example, the second region of the distal portion may be free from the plurality of slots.

Alternatively or additionally to any of the examples above, in another example, the pressure sensor may be positioned proximal to the one or more apertures.

In another example, a pressure sensing guidewire may comprise a tubular member having a proximal portion and a distal portion, wherein the distal portion has a plurality of slots formed therein. The distal portion may have a first wall thickness along a first region and a second wall thickness smaller than the first wall thickness along a second region. The pressure sensing guidewire may further comprise a pressure sensor disposed within the distal portion of the tubular member and housed within the second region and an anti-thrombogenic coating disposed on an outer surface of the second region of the distal portion of the tubular member.

Alternatively or additionally to any of the examples above, in another example, the anti-thrombogenic coating may comprise a hydrophilic coating.

Alternatively or additionally to any of the examples above, in another example, the hydrophilic coating may comprise a heparinized hydrophilic coating.

Alternatively or additionally to any of the examples above, in another example, the anti-thrombogenic coating may comprise a hydrophobic coating.

Alternatively or additionally to any of the examples above, in another example, the hydrophobic coating may comprise silicone.

Alternatively or additionally to any of the examples above, in another example, the hydrophobic coating may be disposed on the pressure sensor.

Alternatively or additionally to any of the examples above, in another example, the first region of the distal portion may be disposed proximal to the second region of the distal portion.

In another example, a pressure sensing guidewire may comprise a tubular member having a proximal portion and a distal portion, wherein the distal portion has a plurality of slots formed therein. The distal portion may have a first wall thickness along a first region and a second wall thickness smaller than the first wall thickness along a second region. The pressure sensing guidewire may further comprise a pressure sensor disposed within the distal portion of the tubular member and housed within the second region and an anti-thrombogenic coating disposed on an inner surface and an outer surface of the second region of the distal portion of the tubular member.

Alternatively or additionally to any of the examples above, in another example, the anti-thrombogenic coating may comprise a heparinized hydrophilic coating.

Alternatively or additionally to any of the examples above, in another example, the anti-thrombogenic coating may comprise silicone.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 1A-1C are close up partial cross-sectional side views of a portion of the example medical device of FIG. 1.

Figure 1:
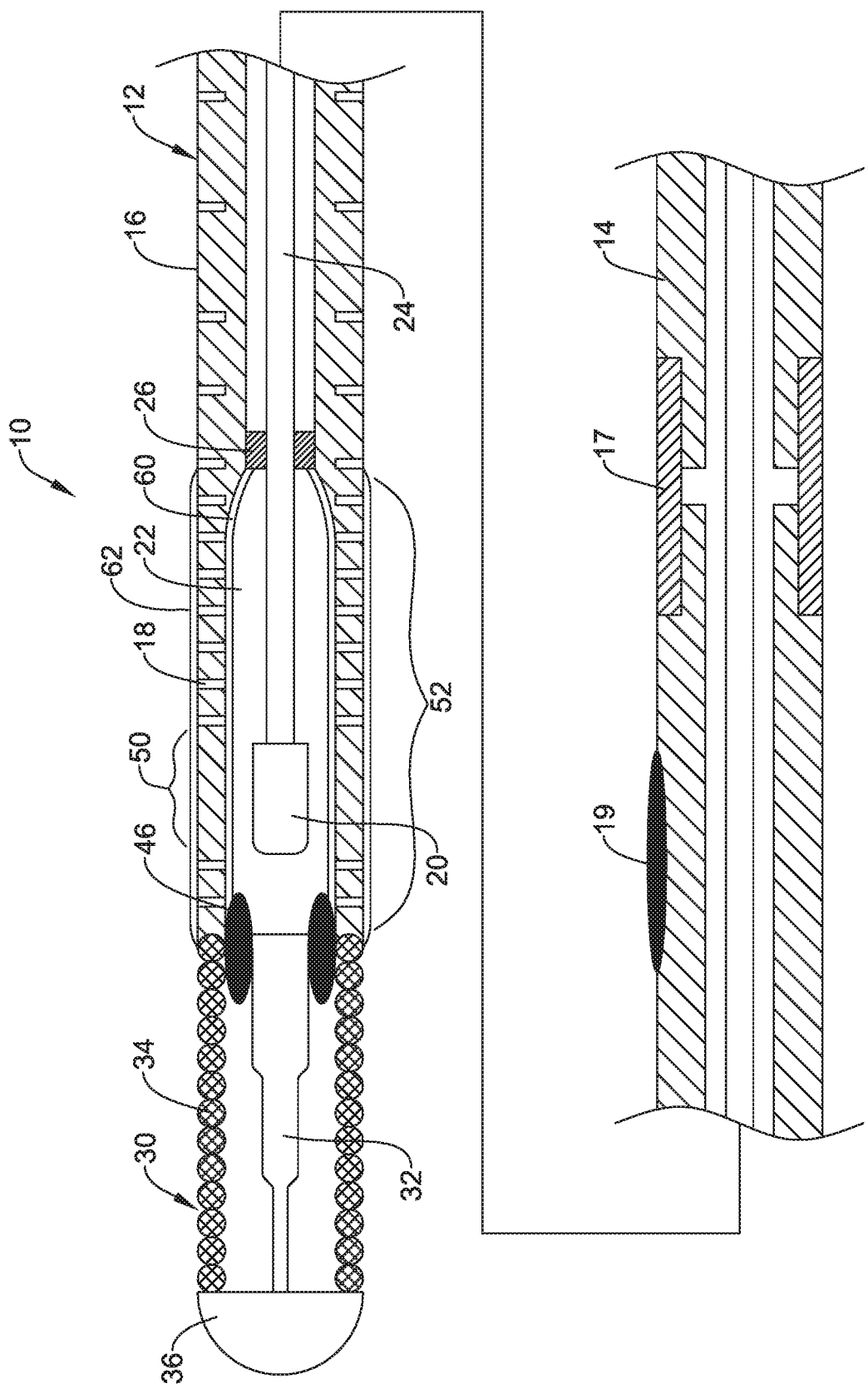
FIG. 1 is a partial cross-sectional side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the ratio of the pressure after or distal of a stenosis (e.g., $P_d$) relative to the pressure before the stenosis and/or the aortic pressure (e.g., $P_a$). In other words, FFR may be understood as $P_d/P_a$.

FIG. 1 illustrates a portion of an example medical device 10. In this example, medical device 10 is a blood pressure sensing guidewire 10. However, this is not intended to be limiting as other medical devices are contemplated including, for example, catheters, shafts, leads, wires, or the like. Guidewire 10 may include a tubular member or shaft 12. Shaft 12 may include a proximal portion 14 and a distal portion 16. The materials for proximal portion 14 and distal portion 16 may vary and may include those materials disclosed herein. For example, distal portion 16, proximal portion 14, or both may include a nickel-cobalt-chromium-molybdenum alloy (e.g., MP35-N), stainless steel, a nickel-titanium alloy (e.g., nitinol), combinations thereof, or other suitable materials including those materials disclosed herein. These are just examples. Other materials may also be utilized.

In some embodiments, proximal portion 14 and distal portion 16 are formed from the same monolith of material. In other words, proximal portion 14 and distal portion 16 are portions of the same tube defining shaft 12. In other embodiments, proximal portion 14 and distal portion 16 are separate tubular members that are joined together. For example, a section of the outer surface of portions 14/16 may be removed and a sleeve 17 may be disposed over the removed sections to join portions 14/16. Alternatively, sleeve 17 may be simply disposed over portions 14/16. Other bonds may also be used including welds, thermal bonds, adhesive bonds, or the like. If utilized, sleeve 17 used to join proximal portion 14 with distal portion 16 may include a material that desirably bonds with both proximal portion 14 and distal portion 16. For example, sleeve 17 may include a nickel-chromium-molybdenum alloy (e.g., INCONEL).

A plurality of slots 18 may be formed in tubular member 12. In at least some embodiments, slots 18 are formed in distal portion 16. In at least some embodiments, proximal portion 14 lacks slots 18. However, proximal portion 14 may include slots 18. Slots 18 may be desirable for a number of reasons. For example, slots 18 may provide a desirable level of flexibility to tubular member 12 (e.g., along distal portion 16) while also allowing suitable transmission of torque. Slots 18 may be arranged/distributed along distal portion 16 in a suitable manner including any of those arrangements disclosed herein. For example, slots 18 may be arranged as opposing pairs of slots 18 that are distributed along the length of distal portion 16. In some embodiments, adjacent pairs of slots 18 may have a substantially constant spacing relative to one another. Alternatively, the spacing between adjacent pairs may vary. For example, more distal regions of distal portion 16 may have a decreased spacing (and/or increased slot density), which may provide increased flexibility. In other embodiments, more distal regions of distal portion 16 may have an increased spacing (and/or decreased slot density). These are just examples. Other arrangements are contemplated.

A pressure sensor 20 may be disposed within tubular member 12 (e.g., within a lumen 22 of tubular member 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, pressure sensor 20 may include an optical pressure sensor. In at least some of these embodiments, a fiber optic cable 24 may be attached to pressure sensor 20 and may extend proximally therefrom. An attachment member 26 may attach fiber optic cable 24 to tubular member 12. Attachment member 26 may be circumferentially disposed about and attached to optical fiber 24 and may be secured to the inner surface of tubular member 12 (e.g., distal portion 16). In at least some embodiments, attachment member 26 is proximally spaced from pressure sensor 20. Other arrangements are contemplated. In some instances, a centering ring (not shown) may be disposed around optical fiber 24 at a position that is spaced proximally from optical pressure sensor 20.

In at least some embodiments, distal portion 16 may include a region with a thinned wall and/or an increased inner diameter that defines a housing region 52. For example, the distal portion 16 may have a first wall thickness along a first region and a different second wall thickness along a second region. In general, housing region 52 is the region of distal portion 16 that ultimately "houses" the pressure sensor (e.g., pressure sensor 20). By virtue of having a portion of the inner wall of tubular member 12 being removed at housing region 52, additional space may be created or otherwise defined that can accommodate sensor 20.

In at least some embodiments, it may be desirable for pressure sensor 20 to have reduced exposure along its side surfaces to fluid pressure (e.g., from the blood). Accordingly, it may be desirable to position pressure sensor 20 along a landing region 50 defined along housing region 52. Landing region 50 may be substantially free of slots 18 so that the side surfaces of pressure sensor 20 have a reduced likelihood of being deformed due to fluid pressures or pressure from landing region 50 at these locations. Distal of landing area 50, housing region 52 may include slots 18 that provide fluid access to pressure sensor 20.

Moreover, slots 18 may define a fluid pathway that allows blood (and/or a body fluid) to flow from a position along the exterior or outer surface of guidewire 10 (and/or tubular member 12), through slots 18, and into the lumen 22 of tubular member 12, where the blood can come into contact with pressure sensor 20. Because of this, no additional side openings/holes (e.g., other than slots 18) may be necessary in tubular member 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20.

In some instances, blood flow through a vessel and/or along portions of a medical device may be reduced. When this occurs, a potential exists for red blood cells to be lysed and/or enzymatic release to occur. Either of these two scenarios could lead to coagulation of blood (e.g., formation of thrombus) including coagulation of blood along a portion of a medical device. It may be desirable to reduce coagulation/thrombus formation along medical devices. For example, coagulation of blood and/or thrombus formation along medical device 10 (e.g., along lumen 22 of medical device 10) may interfere with the sensing capability of pressure sensor 20 and/or lead to measurement drift. It may be desirable to reduce the potential for blood coagulation and/or thrombus formation along medical device 10 (including reducing the potential for blood coagulation and/or thrombus formation along lumen 22).

An anti-thrombogenic coating, such as a hydrophobic or hydrophilic coating, may be disposed on the outer surface and/or inner surface of the housing region 52 to reduce thrombus formation in the lumen 22 and/or on an outer surface of the housing region 52. For example, an inner layer 60 may be disposed on an inner surface of the housing region 52 and an outer layer 62 may be disposed on an outer surface of the housing region 52. In some embodiments, the inner and outer layers 60, 62 may extend proximally and/or distally of the housing region 52, as desired. It is further contemplated that only one of the inner layer 60 or outer layer 62 may be present. The inner layer 60 and the outer layer 62 may be formed of the same material or different materials, as desired. In some instances, the inner layer 60 and/or outer layer 62 may not extend into the slots 18, as shown in FIG. 1A, such that the sidewalls of the slots 18 are free from the coating. In another embodiment, one or both of the inner and outer layers 60, 62 may extend along the walls of the slots 18 such that a continuous coating covers all of the surfaces, including the sidewalls of the slots 18 of the housing region 52, as shown in FIG. 1B. In yet other embodiments, one or both of the inner and outer layers 60, 62 may extend partially into the slots 18 to partially coat the sidewalls of the slots, as shown in FIG. 1C. It is further contemplated that the coating may extend partially or fully along a length of the sidewalls of the slots 18 when only one of the inner or outer layers 60, 62 are present.

In some instances, the inner and/or outer layers 60, 62 may be a medical grade hydrophobic silicone coating. It is contemplated that the coating 60, 62 may be applied as a solution and subsequently cured. In some embodiments, the silicone solution may be a solution of MDX4 manufactured by DOW CORNING®, in the range of 2.5% to 5% MDX4 by weight. In other embodiments, the silicone solution may be a solution of approximately 7% MED-4159 manufactured by NuSil, by weight manufactured by NUSIL TECHNOLOGY. Other medical grade silicones are contemplated, as well as solution concentration of less than 2.5% and greater than 5% by weight. These are just examples. It is contemplated that the guidewire 10 may be assembled, dipped into the silicone solution, and subsequently cured in an oven. In some embodiments, the silicone solution may be applied to the entirety of the housing region 52 as well as the pressure sensor 20.

In other instances, the inner and/or outer layers 60, 62 may be a hydrophilic coating. The hydrophilic coating may additionally contain heparin to actively inhibit thrombus generation, although this is not required. An illustrative heparinized hydrophilic coating may be product number 3477-87 available from SURMODICS. It is contemplated that the hydrophilic coating may be applied to the housing region 52 prior to installing the pressure sensor 20. Once the hydrophilic coating has been applied, the hydrophilic coating may be cured with ultraviolet (UV) light. The pressure sensor 20 may be installed after curing the coating and the guidewire assembly completed.

A tip member 30 may be coupled to distal portion 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal portion 16 of tubular member 12 with a bonding member 46 such as a weld. It is contemplated that the tip member 30 may be coupled to the distal portion 16 before or after application of the hydrophobic or hydrophilic coating 60, 62, as desired.

Tubular member 12 may include a hydrophilic coating 19. In some embodiments, hydrophilic coating 19 may extend along substantially the full length of tubular member 12. In other embodiments, one or more discrete sections of tubular member 12 may include hydrophilic coating 19.

Figure 2:
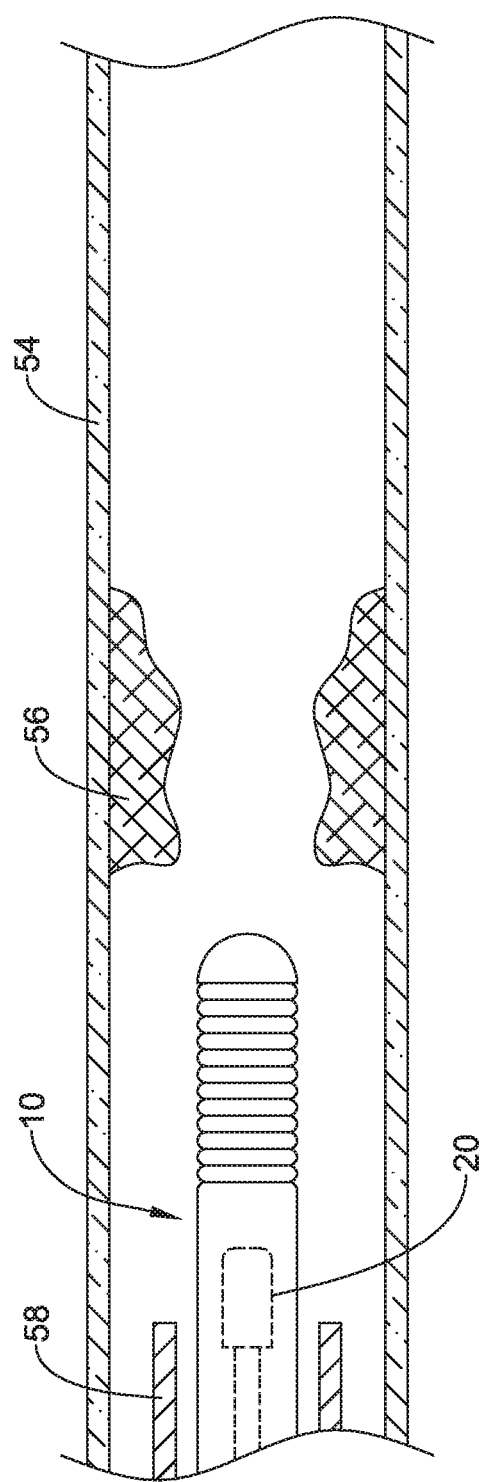
FIG. 2 is a partial cross-sectional view of an example medical device disposed at a first position adjacent to an intravascular occlusion.
Figure 3:
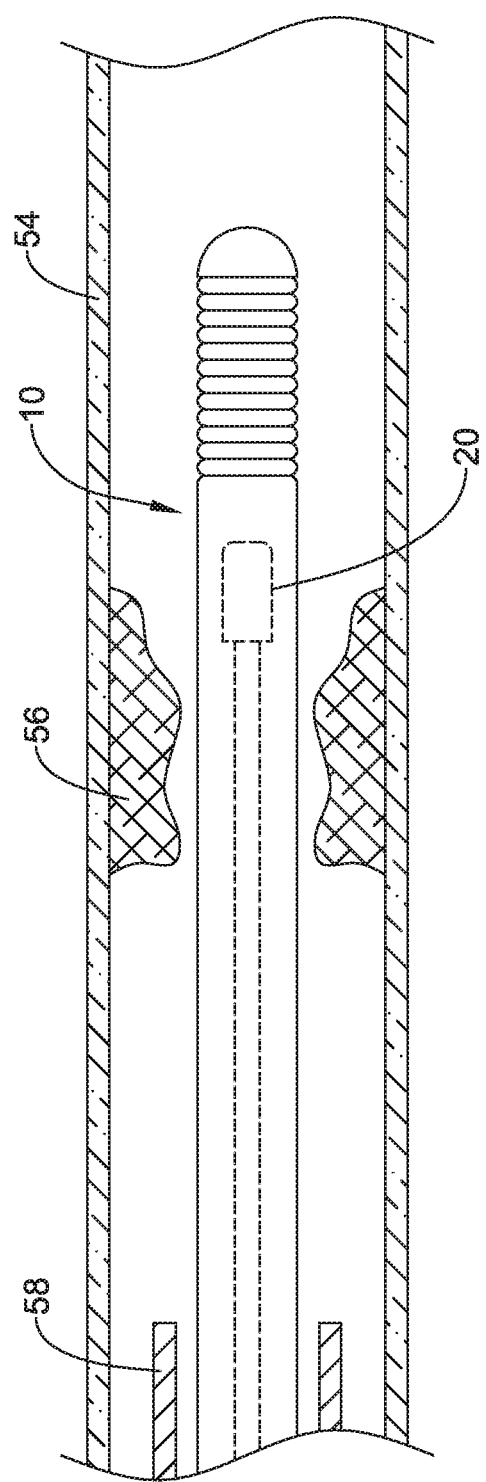
FIG. 3 is a partial cross-sectional view of an example medical device disposed at a second position adjacent to an intravascular occlusion.

In use, a clinician may use guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire 10 through a blood vessel or body lumen 54 to a position that is proximal or upstream of an occlusion 56 as shown in FIG. 2. For example, guidewire 10 may be advanced through a guide catheter 58 to a position where at least a portion of sensor 20 is disposed distal of the distal end of guide catheter 58 and measuring the pressure within body lumen 54. This pressure may be characterized as an initial pressure. In some embodiments, the aortic pressure may also be measured by another device (e.g., a pressure sensing guidewire, catheter, or the like). The initial pressure may be equalized with the aortic pressure. For example, the initial pressure measured by guidewire 10 may be set to be the same as the measured aortic pressure. Guidewire 10 may be further advanced to a position distal or downstream of occlusion 56 as shown in FIG. 3 and the pressure within body lumen 54 may be measured. This pressure may be characterized as the downstream or distal pressure. The distal pressure and the aortic pressure may be used to calculate FFR.

Figure 4:
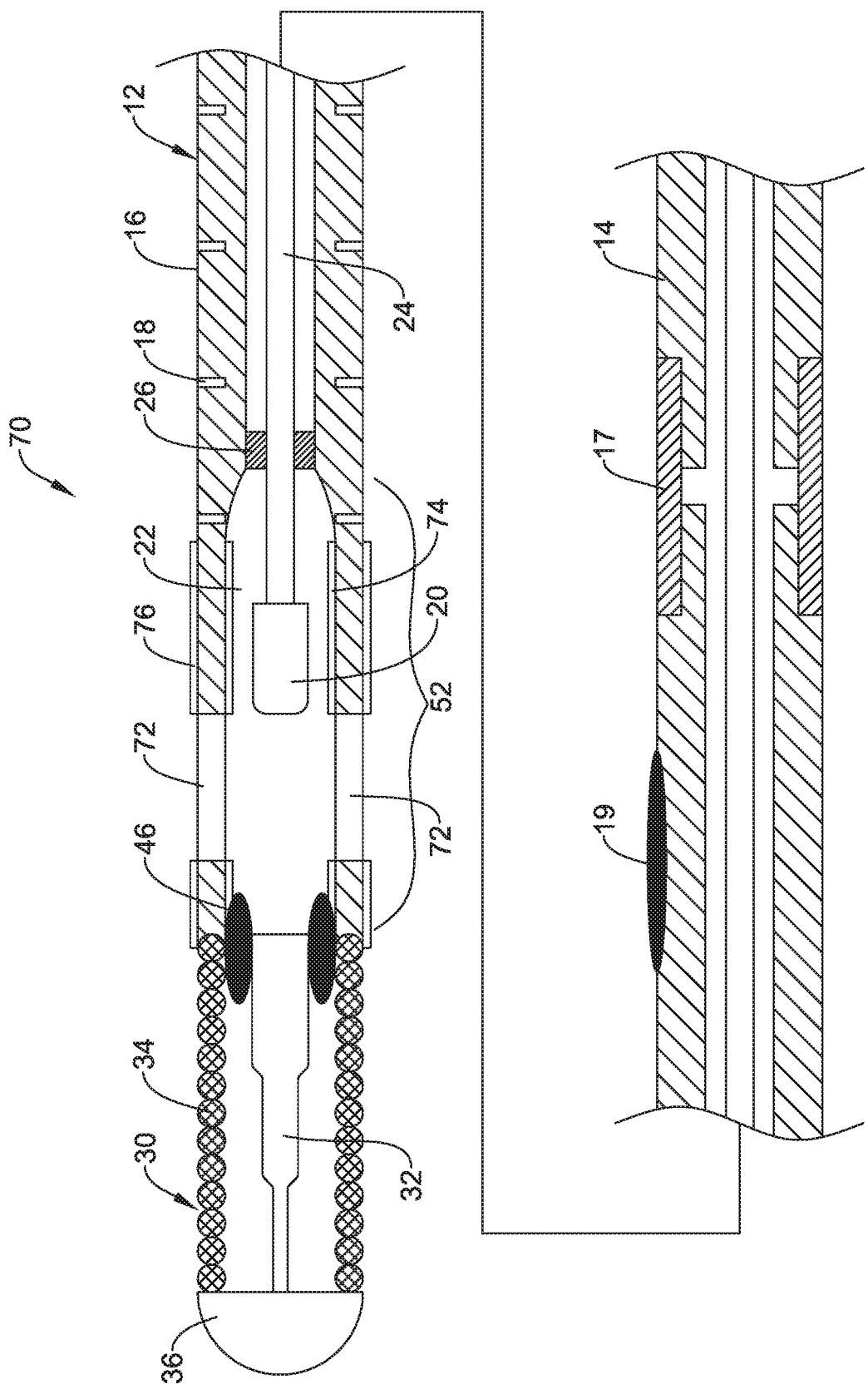
FIG. 4 is a partial cross-sectional side view of a portion of another example medical device.

FIG. 4 illustrates a portion of another example medical device 70. In this example, the medical device 70 is a blood pressure sensing guidewire 70. However, this is not intended to be limiting as other medical devices are contemplated including, for example, catheters, shafts, leads, wires, or the like. The guidewire 70 may be similar in form and function to the guidewire described above 10. Guidewire 70 may include a tubular member or shaft 12. Shaft 12 may include a proximal portion 14 and a distal portion 16.

In some embodiments, proximal portion 14 and distal portion 16 are formed from the same monolith of material. In other words, proximal portion 14 and distal portion 16 are portions of the same tube defining shaft 12. In other embodiments, proximal portion 14 and distal portion 16 are separate tubular members that are joined together. For example, a section of the outer surface of portions 14/16 may be removed and a sleeve 17 may be disposed over the removed sections to join portions 14/16. Alternatively, sleeve 17 may be simply disposed over portions 14/16. Other bonds may also be used including welds, thermal bonds, adhesive bonds, or the like. If utilized, sleeve 17 used to join proximal portion 14 with distal portion 16 may include a material that desirably bonds with both proximal portion 14 and distal portion 16.

A plurality of slots 18 may be formed in tubular member 12. In at least some embodiments, slots 18 are formed in distal portion 16. In at least some embodiments, proximal portion 14 lacks slots 18. However, proximal portion 14 may include slots 18. Slots 18 may be desirable for a number of reasons. For example, slots 18 may provide a desirable level of flexibility to tubular member 12 (e.g., along distal portion 16) while also allowing suitable transmission of torque. Slots 18 may be arranged/distributed along distal portion 16 in a suitable manner including any of those arrangements disclosed herein. For example, slots 18 may be arranged as opposing pairs of slots 18 that are distributed along the length of distal portion 16. In some embodiments, adjacent pairs of slots 18 may have a substantially constant spacing relative to one another. Alternatively, the spacing between adjacent pairs may vary. For example, more distal regions of distal portion 16 may have a decreased spacing (and/or increased slot density), which may provide increased flexibility. In other embodiments, more distal regions of distal portion 16 may have an increased spacing (and/or decreased slot density). These are just examples. Other arrangements are contemplated.

A pressure sensor 20 may be disposed within tubular member 12 (e.g., within a lumen 22 of tubular member 12). While pressure sensor 20 is shown schematically in FIG. 4, it can be appreciated that the structural form and/or type of pressure sensor 20 may vary. For example, pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, pressure sensor 20 may include an optical pressure sensor. In at least some of these embodiments, a fiber optic cable 24 may be attached to pressure sensor 20 and may extend proximally therefrom. An attachment member 26 may attach fiber optic cable 24 to tubular member 12. Attachment member 26 may be circumferentially disposed about and attached to optical fiber 24 and may be secured to the inner surface of tubular member 12 (e.g., distal portion 16). In at least some embodiments, attachment member 26 is proximally spaced from pressure sensor 20. Other arrangements are contemplated. In some instances, a centering ring (not shown) may be disposed around optical fiber 24 at a position that is spaced proximally from optical pressure sensor 20.

In at least some embodiments, distal portion 16 may include a region with a thinned wall and/or an increased inner diameter that defines a housing region 52. In general, housing region 52 is the region of distal portion 16 that ultimately "houses" the pressure sensor (e.g., pressure sensor 20). By virtue of having a portion of the inner wall of tubular member 12 being removed at housing region 52, additional space may be created or otherwise defined that can accommodate sensor 20.

In some instances, the housing region 52 may include one or more apertures 72 in place of or in addition to slots 18 for allowing fluid to enter the lumen 22 and access to pressure sensor 20. In at least some embodiments, it may be desirable for pressure sensor 20 to have reduced exposure along its side surfaces to fluid pressure (e.g., from the blood). Accordingly, it may be desirable to position pressure sensor 20 proximal to or distal to the one or more apertures 72. The housing region 52 may be substantially free from apertures 72 and/or slots 18 in the region adjacent to the pressure sensor.

It is contemplated that when two or more apertures 72 are provided, the apertures 72 may be uniformly spaced about a circumference of the housing region 52. For example, when two apertures 72 are provided, the apertures 72 may be positioned approximately 180° from one another about the circumference and at a similar axial location, as shown in FIG. 4. This is just an example. The apertures 72 may be positioned at any circumferential and/or axial location desired. It is further contemplated that the apertures 72 need not be uniformly positioned about the circumference. In some instances, the apertures 72 may be eccentrically arranged. The apertures 72 may take any shape desired, such as, but not limited to: circular, oval, square, rectangular, polygonal, etc.

In some instances, blood flow through a vessel and/or along portions of a medical device may be reduced. When this occurs, a potential exists for red blood cells to be lysed and/or enzymatic release to occur. Either of these two scenarios could lead to coagulation of blood (e.g., formation of thrombus) including coagulation of blood along a portion of a medical device. It may be desirable to reduce coagulation/thrombus formation along medical devices. For example, coagulation of blood and/or thrombus formation along medical device 70 (e.g., along lumen 22 of medical device 70) may interfere with the sensing capability of pressure sensor 20 and/or lead to measurement drift. It may be desirable to reduce the potential for blood coagulation and/or thrombus formation along medical device 70 (including reducing the potential for blood coagulation and/or thrombus formation along lumen 22).

A hydrophobic or hydrophilic coating may be disposed on the outer surface and/or inner surface of the housing region 52 to reduce thrombus formation in the lumen 22 and/or on an outer surface of the housing region 52. For example, an inner layer 74 may be disposed on an inner surface of the housing region 52 and an outer layer 76 may be disposed on an outer surface of the housing region 52. In some embodiments, the inner and outer layers 74, 76 may extend proximally and/or distally of the housing region 52, as desired. It is further contemplated that only one of the inner layer 74 or outer layer 76 may be present. The inner layer 74 and the outer layer 76 may be formed of the same material or different materials, as desired. In some instances, the inner layer 74 and/or outer layer 76 may not extend into the apertures 72 and/or slots 18 in similar to the embodiment shown in FIG. 1A, such that the apertures 72 and/or slots 18 are free from the coating. In another embodiment, one or both of the inner and outer layers 74, 76 may extend along the walls of the apertures 72 and/or slots 18 such that a continuous coating covers all of the surfaces of the housing region 52, similar to the embodiment shown in FIG. 1B. In yet other embodiments, one or both of the inner and outer layers 74, 76 may extend partially into the apertures 72 and/or slots 18, similar to the embodiment shown in FIG. 1C.

In some instances, the inner and/or outer layers 74, 76 may be a medical grade hydrophobic silicone coating. It is contemplated that the coating 74, 76 may be applied as a solution and subsequently cured. In some embodiments, the silicone solution may be a solution of MDX4 manufactured by DOW CORNING®, in the range of 2.5% to 5% MDX4 by weight. In other embodiments, the silicone solution may be a solution of approximately 7% NuSil by weight manufactured by NUSIL TECHNOLOGY. Other medical grade silicones are contemplated, as well as solution concentrations of less than 2.5% and greater than 5% by weight. These are just examples. It is contemplated that the guidewire 70 may be assembled, dipped into the silicone solution, and subsequently cured in an oven. In some embodiments, the silicone solution may be applied to the entirety of the housing region 52 as well as the pressure sensor 20.

In other instances, the inner and/or outer layers 74, 76 may be a hydrophilic coating. The hydrophilic coating may additionally contain heparin to actively inhibit thrombus generation, although this is not required. An illustrative heparinized hydrophilic coating may be product number 3477-87 available from SURMODICS. It is contemplated that the hydrophilic coating may be applied to the housing region 52 prior to installing the pressure sensor 20. Once the hydrophilic coating has been applied, the hydrophilic coating may be cured with ultraviolet (UV) light. The pressure sensor 20 may then be installed after curing the coating and the guidewire assembly completed.

A tip member 30 may be coupled to distal portion 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal portion 16 of tubular member 12 with a bonding member 46 such as a weld. It is contemplated that the tip member 30 may be coupled to the distal portion 16 before or after application of the hydrophobic or hydrophilic coating 74, 76, as desired.

Tubular member 12 may include a hydrophilic coating 19. In some embodiments, hydrophilic coating 19 may extend along substantially the full length of tubular member 12. In other embodiments, one or more discrete sections of tubular member 12 may include hydrophilic coating 19.

It can be appreciated that an FFR system that utilizes an optical pressure sensor in a pressure sensing guidewire may be connected to a number of processing/conditioning units, displays, and the like. When making these connections, the various cables/connections may be designed so that the optical signals can be transmitted between adjacent optical fibers in an efficient manner.

A wide variety of optical connectors exist that are designed to allow for efficient communication between adjacent optical fibers. Such connectors are typically utilized in industries such as telecommunication. The use of optical fibers in medical devices provides a variety of new challenges. When optical fibers are utilized in medical devices, the connectors may need to allow for the connection of various devices and/or components while allowing for movement (e.g., rotation) of the components relative to one another during use. These movements could lead to complications. For example, the polished end surfaces of the fiber could contact one another, which could ultimately scratch, rub, or damage the fibers. This could impact the optical communication between the fibers. At least some of the medical devices, medical device systems, and connectors disclosed herein may include features that improve the connection of components of a fiber optic system such as the connection of optical fibers.

For the purposes of this disclosure, reference will be made to "medical device systems". The medical device systems may be understood to be one or more medical devices that may be used together. In at least some embodiments, the medical device systems disclosed herein may be systems for measuring FFR. These systems may include a pressure sensing guidewire, an optical connector cable coupled to the guidewire, a signal conditioning unit and/or processing unit coupled to the optical connector cable, and a display unit or output. The systems may also include additional intermediate cables and/or devices, guide catheters, other pressure measuring devices and/or components, and the like. References made to a system are not meant to imply that all of these components are present.

The materials that can be used for the various components of guidewire 10 (and/or other guidewires disclosed herein) and the various tubular members disclosed herein may include those commonly associated with medical devices. For simplicity purposes, the following discussion makes reference to tubular member 12 and other components of guidewire 10. However, this is not intended to limit the devices and methods described herein, as the discussion may be applied to other similar tubular members and/or components of tubular members or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A pressure sensing guidewire, comprising:
a tubular member having a proximal portion and a distal portion;
wherein the distal portion has a plurality of slots formed therein and two or more apertures formed therein, the two or more apertures positioned uniformly about a circumference of the distal portion and at similar axial locations distal to the plurality of slots;
wherein the distal portion has a first wall thickness along a first region and a second wall thickness smaller than the first wall thickness along a second region;
a pressure sensor disposed within the distal portion of the tubular member and housed within the second region distal to the plurality of slots; and
an anti-thrombogenic coating disposed on an inner surface of the second region of the distal portion of the tubular member and at least partially covering one or more side walls of the two or more apertures;
wherein the first region of the distal portion of the tubular member is free from the anti-thrombogenic coating.

2. The pressure sensing guidewire of claim 1, wherein the anti-thrombogenic coating comprises a hydrophilic coating.

3. The pressure sensing guidewire of claim 2, wherein the hydrophilic coating comprises a heparinized hydrophilic coating.

4. The pressure sensing guidewire of claim 1, wherein the anti-thrombogenic coating comprises a hydrophobic coating.

5. The pressure sensing guidewire of claim 4, wherein the hydrophobic coating comprises silicone.

6. The pressure sensing guidewire of claim 4, wherein the hydrophobic coating is disposed on the pressure sensor.

7. The pressure sensing guidewire of claim 1, wherein the first region of the distal portion is disposed proximal to the second region of the distal portion.

8. The pressure sensing guidewire of claim 1, wherein the second region of the distal portion is free from the plurality of slots.

9. The pressure sensing guidewire of claim 1, wherein the pressure sensor is positioned proximal to the one or more apertures.

10. A pressure sensing guidewire, comprising:
a tubular member having a proximal portion and a distal portion;
wherein the distal portion has a plurality of slots formed therein and two or more apertures formed therein, the two or more apertures having a length extending parallel to a longitudinal axis of the tubular member and positioned uniformly about a circumference of the distal portion and at similar axial locations distal to the plurality of slots, the length of the two or more apertures greater than a length of the plurality of slots;
wherein the distal portion has a first wall thickness along a first region and a second wall thickness smaller than the first wall thickness along a second region;
a pressure sensor disposed within the distal portion of the tubular member and housed within the second region proximal to the two or more apertures; and
an anti-thrombogenic coating disposed on an outer surface and an inner surface of the second region of the distal portion of the tubular member, wherein sidewalls of the slots are free from the anti-thrombogenic coating or wherein the anti-thrombogenic coating extends partially into the slots to partially coat the sidewalls of the slots;
wherein the first region of the distal portion of the tubular member is free from the anti-thrombogenic coating.

11. The pressure sensing guidewire of claim 10, wherein the anti-thrombogenic coating comprises a hydrophilic coating.

12. The pressure sensing guidewire of claim 11, wherein the hydrophilic coating comprises a heparinized hydrophilic coating.

13. The pressure sensing guidewire of claim 10, wherein the anti-thrombogenic coating comprises a hydrophobic coating.

14. The pressure sensing guidewire of claim 13, wherein the hydrophobic coating comprises silicone.

15. The pressure sensing guidewire of claim 13, wherein the hydrophobic coating is disposed on the pressure sensor.

16. The pressure sensing guidewire of claim 10, wherein the first region of the distal portion is disposed proximal to the second region of the distal portion.

17. A pressure sensing guidewire, comprising:
a tubular member having a proximal portion and a distal portion;
wherein the distal portion has a plurality of slots formed therein and two or more apertures formed therein, the two or more apertures positioned uniformly about a circumference of the distal portion and at similar axial locations distal to the plurality of slots;
wherein the distal portion has a first wall thickness along a first region and a second wall thickness smaller than the first wall thickness along a second region;
a pressure sensor disposed within the distal portion of the tubular member and housed within the second region; and
an anti-thrombogenic coating disposed on an inner surface and an outer surface of the second region of the distal portion of the tubular member and extending along a length of one or more sidewalls of the two or more apertures;
wherein the first region of the distal portion of the tubular member is free from the anti-thrombogenic coating.

18. The pressure sensing guidewire of claim 17, wherein the anti-thrombogenic coating comprises a heparinized hydrophilic coating.

19. The pressure sensing guidewire of claim 17, wherein the anti-thrombogenic coating comprises silicone.

* * * * *